United States Patent [19]

Klemm

[11] Patent Number: Plant 6,704

[45] Date of Patent: Mar. 28, 1989

[54] MINIATURE CARNATION NAMED KLEFITONI

[76] Inventor: Siegfried Klemm, Hanfacker 8, D 7000, Stuttgart 50, Fed. Rep. of Germany

[21] Appl. No.: 116,239

[22] Filed: Nov. 2, 1987

[51] Int. Cl.[4] ..... A01H 5/00
[52] U.S. Cl. ..... Plt./70
[58] Field of Search ..... Plt./70

*Primary Examiner*—James R. Feyrer
*Attorney, Agent, or Firm*—Charles W. Rummler

[57] ABSTRACT

A new spray carnation variety having relatively small, clear, very light yellow blooms produced continuously and appearing alternately at the upper portion of a strong, erect stem, the flowers being distinguished by their clear, overall pale yellow petals and the plant itself being distinguished by its height of about 60 cm. in average and its strong, erect character.

1 Drawing Sheet

BACKGROUND OF THE NEW PLANT

This new spray carnation originated as a sport of the variety 'Loncruso' (U.S. Plant Pat. No. 5,514) grown both in greenhouse and outdoors at my nursery in Stuttgart, West Germany, and this plant was selected for propagation because of the extremely light, clear yellow coloration of its flower petals, the flowers appearing to be of good quality and being carried on strong, upright stems. This sport discovery was reproduced by me under my direction by cuttings with such satisfactory results that I directed further propagation to be carried on through a series of successive generations by cuttings from earlier plants produced in the same manner. This extended propagation of my discovery plant demonstrated clearly that it has a strong and vigorous growth habit, that the flowers have a very good lasting quality, that its growth habit is quite rapid and that the plant is very good for both greenhouse and outdoor culture, these characteristics being fully retained from generation to generation and appearing to be firmly fixed.

DESCRIPTION OF THE DRAWING

My new spray carnation variety is illustrated by the accompanying photographic drawing, which shows the flowering portion of a typical stem in full color, the stem bearing buds and flowers at various stages of growth, the view also including a series of separated petals and single buds in four stages of opening, the colors shown being as nearly true to those specified herein as is reasonably possible to obtain by conventional photographic procedures.

DESCRIPTION OF THE NEW PLANT

The following is a detailed description of my new spray carnation plant based upon observations of plants grown at Stuttgart, West Germany, the color designations being according to the R.H.S. Colour Chart published by The Royal Horticultural Society of London, England.

THE PLANT

Origin: Sport.
Parentage: The carnation variety 'Loncruso' (U.S. Plant Pat. No. 5,514).
Classification:

*Botanic.*—*Dianthis caryophyllus.*
*Commercial.*—Spray carnation.
Form: Bush of strong, erect character.
Height: About 60 cm., in average.
Branching: Normal.
Growth: Quite rapid, sturdy and upright.
Foliage:
*Quality.*—Moderate.
*Number of leaves.*—About 16 per stem in the summertime.
*Leaf size.*—About 7 cm. long and about 0.8 cm. wide.
*Shape.*—Oblong, outwardly curled and with entire margins.
*Texture.*—Smooth.
*Color.*—Blue-Green on both upper and under sides.
*Leaflets.*—None.
*Ribs and veins.*—Not noticeable.

THE BUD

Size: Medium.
*Diameter.*—About 15 mm.
*Length.*—About 35 to 40 mm.
Shape: Ovoid.
Rate of opening: Moderate.
Color of petals: When sepals first divide and petals begin to unfurl: Light Yellow, RHS 1-D.
Sepals:
*Number.*—Five.
*Shape.*—Joined together at the lower part with the upper portion being somewhat oval in shape and having an acute apex. The sepals are hooded over the bud before dividing and continue to stand up as the flower opens.
*Color.*—Gray-Green both inside and outside.
Calyx: Small and generally cylindrical inverted bell in shape.
*Size.*—About 15 mm. in diameter and about 20 mm. long.
*Splitting.*—The calyx does not split.
*Aspect.*—Smooth.
Character of flower stem: Erect.
*Aspect.*—Gray-Green.

THE FLOWER

Blooming habit: Continuous the year around.
Size of bloom: Medium.

*Diameter.*—About 45 to 55 mm.

*Depth.*—About 40 mm., in average.

Borne: Singly, on stems of various lengths appearing alternately along the upper portion of the main stem.

Shape: When the bloom first opens and as it matures: High-centered.

Petalage;

*Number of petals.*—About 35 to 42.

*Arrangement.*—Imbricated.

*Form.*—Fan-shaped with serrated margin.

*Texture.*—Soft.

*Aspect.*—Shiny.

*Color.*—All petals, both inside and outside surfaces: Very Pale Yellow, RHS 1-D; or Chartreuse Green, HCC 663/2.

Flower stem:

*Length.*—Averages about 45 to 60 cm.

*Color.*—Gray-Green.

*Character.*—Sturdy and upright.

Effect of weather: None. The plant is extremely good under outside growing conditions.

Fragrance: None

Persistence: The petals hang on and dry and the bloom stays upright.

Lasting quality:

*On plant.*—About 15 days.

*As a cut flower.*—About 12 days in normal vase keeping.

THE REPRODUCTIVE ORGANS

Stamens:

*Number.*—4 or 5.

*Arrangement.*—Around the pistil.

*Anthers.*—Anthers and pollen are rarely present.

Pistils:

*Number.*—One.

*Styles.*—Color: Yellowish white.

*Stigma.*—Color: Yellow.

THE FRUIT

Fertility: The fruit is fertile.

Shape: Ovoid.

Color at maturity: Green-Brown.

This new carnation plant most nearly resembles the parent plant 'Loncruso', this new plant being a fast growing miniature carnation particularly distinguished from its parent by its very light and clear yellow color, its good spray formation, and its extremely good character for growing outdoors.

I claim:

1. The new spray carnation cultivar and the parts thereof, substantially as herein shown and described, characterized by the very light clear yellow coloration of the flower petals, by its relatively fast growth habit and by its very good growth characteristics for outdoor culture.

* * * * *

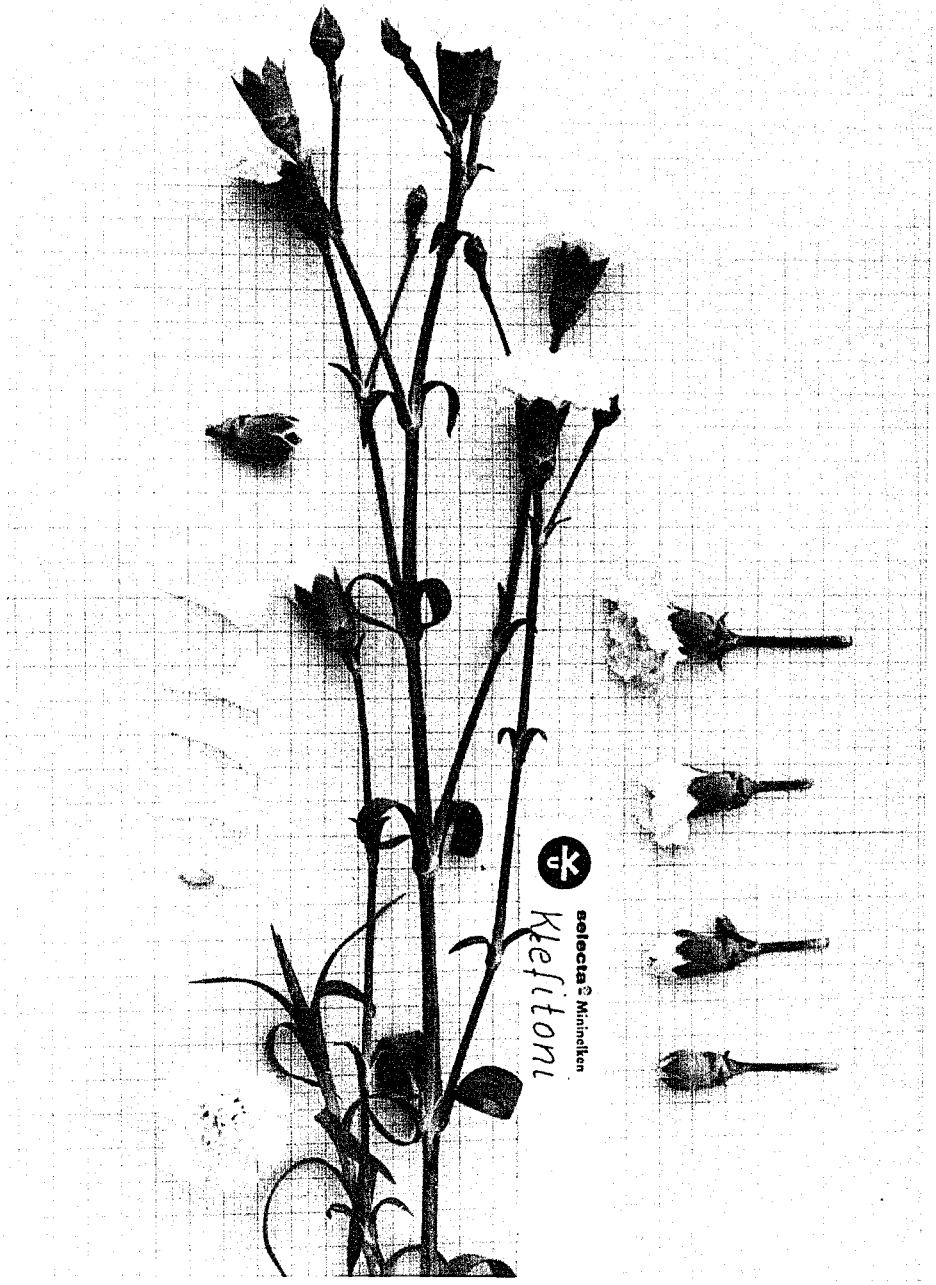
selecta Minniken
Klefitoni